United States Patent
Tziviskos et al.

(10) Patent No.: US 6,505,076 B2
(45) Date of Patent: Jan. 7, 2003

(54) WATER-RESISTANT, WIDEBAND MICROPHONE SUBASSEMBLY

(75) Inventors: George Tziviskos, Encino, CA (US); W. Gary Sokolich, Newport Beach, CA (US); Scott Crawford, Castaic, CA (US); Lee F. Hartley, Castaic, CA (US)

(73) Assignee: Advanced Bionics Corporation, Sylmar, CA (US)

(*) Notice: Subject to any disclaimer, the term of this patent is extended or adjusted under 35 U.S.C. 154(b) by 130 days.

(21) Appl. No.: 09/733,736

(22) Filed: Dec. 8, 2000

(65) Prior Publication Data

US 2002/0177883 A1 Nov. 28, 2002

(51) Int. Cl.[7] .............................................. H04R 25/00
(52) U.S. Cl. ........................ 607/57; 607/55; 381/328; 381/330
(58) Field of Search .............................. 607/57, 55, 56, 607/136, 137; 600/25; 381/312, 322, 328, 330

(56) References Cited

U.S. PATENT DOCUMENTS

| | | | |
|---|---|---|---|
| 4,267,410 A | 5/1981 | Forster et al. | |
| 4,428,377 A | 1/1984 | Zollner et al. | |
| 4,532,930 A | 8/1985 | Crosby et al. | |
| 4,696,287 A | 9/1987 | Hortmann et al. | |
| 5,282,858 A | * 2/1994 | Bisch et al. .............. 600/25 X |
| 5,603,726 A | 2/1997 | Schulman et al. | |
| 5,784,471 A | 7/1998 | Bebenroth | |
| 5,814,095 A | 9/1998 | Muller et al. | |
| 5,824,022 A | 10/1998 | Zilberman et al. | |
| 5,897,486 A | * 4/1999 | Ball et al. ...................... 600/25 |
| 6,075,867 A | * 6/2000 | Bay et al. ..................... 381/191 |
| 6,216,040 B1 | 4/2001 | Harrison | |
| 6,259,951 B1 | * 7/2001 | Kuzma et al. ................. 607/57 |

OTHER PUBLICATIONS

US 5,730,699, 3/1998, Adams et al. (withdrawn)

* cited by examiner

*Primary Examiner*—Kevin Lee
(74) *Attorney, Agent, or Firm*—Kenneth L. Green; Bryant R. Gold (57) ABSTRACT

A moisture-resistant, wideband microphone subassembly for a Behind-The-Ear (BTE) hearing device, provides a barrier to perspiration and rain, while maintaining a good frequency response. The microphone subassembly is contained in the case of the BTE hearing device and comprises a microphone, a boot, and a moisture-resistant membrane. The boot structurally supports the microphone, provides a moisture seal around the microphone case, and provides the microphone with isolation from vibrations in the case of the BTE hearing device. The membrane resists the passage of moisture, while providing an acoustic window permitting sound waves to reach the microphone. In one embodiment high compliance washers sandwich the membrane to improve frequency response. A preferred embodiment provides a substantially flat acoustic frequency response to beyond 10 KHz.

50 Claims, 6 Drawing Sheets

WATER-RESISTANT, WIDEBAND MICROPHONE SUBASSEMBLY

BACKGROUND OF THE INVENTION

The present invention relates to hearing devices for aiding the hearing impaired and the profoundly deaf, and more particularly to a water-resistant microphone subassembly providing isolation from case-born vibrations, and wide band frequency response, for use in a Behind-The-Ear (BTE) hearing system. Such BTE system may form part of a cochlear stimulation system.

Cochlear stimulation systems are known in the art. Such systems are used to help the profoundly deaf (those whose middle and/or outer ear is dysfunctional, but whose auditory nerve remains intact) to hear. The sensation of hearing is achieved by directly exciting the auditory nerve with controlled impulses of electrical current, which impulses are generated as a function of transduced acoustic energy. The acoustic energy is picked up by a microphone carried externally (not implanted) by the person using the device and converted to electrical signals. The electrical signals, in turn, are processed and conditioned by a signal receiver and processor, also referred to as a Wearable Processor (WP), in an appropriate manner, e.g., converted to a sequence of pulses of varying width and/or amplitude. The sequence of pulses, or command words that define such sequence of pulses, is carried by an external cable running from the WP to an external headpiece positioned on the side of the patient's head. A magnet in the headpiece holds the headpiece in place on the head of the user. Such magnet also aligns the headpiece with a corresponding magnet in the an Implantable Cochlear System (ICS). Such ICS receives the command words or pulse sequence, and converts them to appropriate stimulation current pulses that are applied to the auditory nerve through an electrode array implanted in the cochlea, as is known in the art.

While known ICS systems have succeeded in providing the sensation of hearing to the profoundly deaf, they unfortunately also have the disadvantage of appearing unsightly due to the external cable running from the WP to the headpiece positioned on the side of the user's head.

The WP is typically worn or carried by the user on a belt or in a pocket. While the WP is not too large, it is likewise not extremely small, and hence also represents an inconvenience for the user. The cable which connects the WP with the headpiece is often a source of irritation and self-consciousness for the user.

The above-described aesthetic considerations and inconvenience of an external wire are addressed by U.S. Pat. No. 5,824,022, issued Oct. 20, 1998, for "Cochlear stimulation system employing Behind-The-Ear (BTE) Speech Processor With Remote Control." The '022 patent teaches a small single external device that performs the functions of both the WP and the headpiece. The external device is positioned behind the ear to minimize its visibility, and requires no cabling to additional components. The '022 patent is incorporated herein by reference.

While the BTE device taught by the '022 patent resolves the issues of aesthetics and inconvenience, the resulting device, and known BTE hearing aids, disadvantageously expose the microphone to perspiration and rain, resulting in frequent failures. Therefore, there is a need for a microphone assembly that provides resistance to moisture, while maintaining a good frequency response.

SUMMARY OF THE INVENTION

The present invention addresses the above and other needs by providing a moisture-resistant microphone subassembly for Behind-The-Ear (BTE) hearing devices, with a substantially flat frequency response to 10 KHz. The microphone subassembly is comprised primarily of a microphone, a boot, and a moisture-resistant membrane. The microphone has an transducer aperture through which sound waves enter the microphone. The boot includes a microphone cavity and a sound port. The boot structurally supports the microphone, provides the microphone with isolation from vibrations in the case of the BTE device, and provides a seal against moisture seeping around the microphone body and into the transducer aperture of the microphone. The membrane resides in the microphone cavity between sound port and the transducer aperture, and resists the passage of moisture, while permitting sound waves to reach the transducer aperture.

In accordance with one aspect of the invention, a boot provides structural support to the microphone. The boot is made from a high compliance material and isolates the microphone from vibrations that might otherwise create false signals. In the absence of such isolation, events such as rubbing the case of the BTE device against hair or skin, could produce undesirable signals.

It is a feature of the present invention to provide a boot which includes a sound waves port and an microphone cavity. The microphone is situated in the microphone cavity. The fit of the microphone inside the microphone cavity provides a seal against moisture. The sound waves port connects with the microphone cavity to provide an acoustic path for sound waves (acoustic waves) to enter the transducer aperture of the microphone.

It is an additional feature of the present invention to provide a means for retaining the microphone in the microphone cavity. In one embodiment, the boot includes boot fingers at the rear of the microphone cavity. Once the microphone has been pushed into the microphone cavity, the boot fingers hold the microphone in place. In another embodiment, the boot includes a retaining flange around the rear of the microphone cavity. The compliance of the boot material allows the retaining flange to stretch to allow the microphone to be pushed into the microphone cavity. Once the microphone is in the microphone cavity, the retaining flange closes around the rear of the microphone to retain the microphone in the microphone cavity.

It is a further feature of the invention to provide a moisture-resistant membrane. The membrane separates the microphone from the environment and prevents moisture from reaching the microphone, but allows sound waves to reach the microphone. In a preferred embodiment, the membrane provides a stable, flat, wideband acoustic frequency response for the microphone subassembly. Advantageously, the resulting response is flat to beyond 10 KHz.

It is additionally a feature of the present invention that the microphone subassembly fit within a cavity of a BTE case. The cavity is located inside a front surface of the BTE device case, and includes a microphone port in the front surface to allow sound waves access to the microphone subassembly. A water deflector or shield is located just above the BTE sound port to deflect water from the microphone port.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The moisture-resistant microphone subassembly of the present invention provides Behind-The-Ear (BTE) hearing devices with improved performance and reliability. A BTE hearing device 10 is shown carried and resting on an ear 12 of a user in FIG. 1. The BTE device 10 may either be a standard hearing aid, or the external electronics for an Implantable Cochlear Stimulation (ICS) system. In either case, a microphone is required to receive acoustic energy (i.e., sound waves) and convert the acoustic energy into an electronical signal for further processing. In order to receive the acoustic energy, the microphone must be open to at least some extent to the environment.

Figure 1:
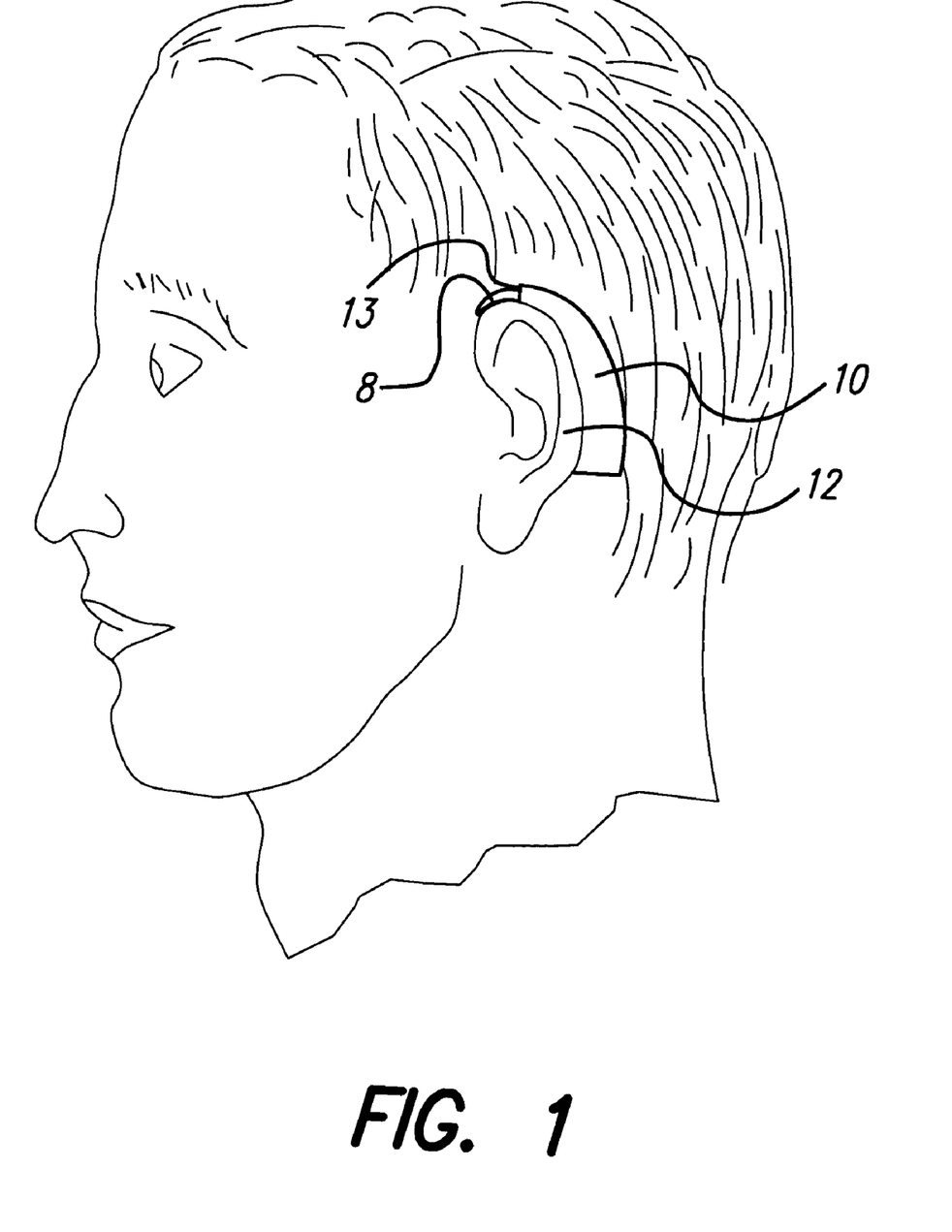
FIG. 1 depicts a typical Behind-The-Ear (BTE) hearing device on a user.

As can be seen in FIG. 1, the BTE hearing device 10 forms an arch that starts behind the ear 12 and reaches over the ear 12. The BTE hearing device 10 ends near the top of the arch, and an earhook 8 continues the arch a short distance. In typical BTE hearing devices, the microphone resides in the BTE device 10 near the highest point of the arch, behind a microphone port 13. While the microphone port 13 is advantageously positioned to receive sound in a natural manner (i.e., from the direction the patient is looking), the position also exposes the microphone to various moisture sources. Such moisture sources include rain, splashed water, perspiration, etc. Such moisture may not only degrade a microphone's performance, but in some instances it may render the hearing device inoperable.

Figure 2:
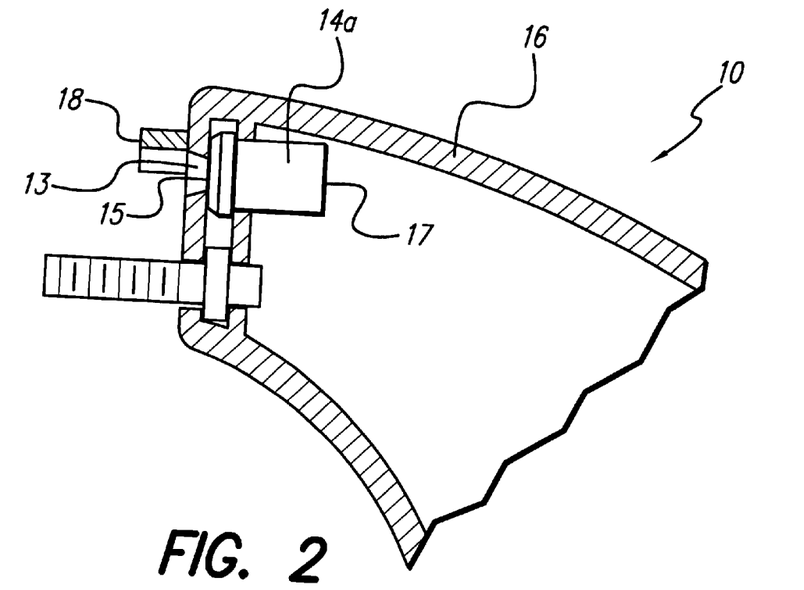
FIG. 2 shows a microphone subassembly in the case of a BTE hearing device.

A cross-section of a portion of a BTE device case 16 is shown in FIG. 2. A microphone subassembly 14a is positioned directly behind the microphone port 13. A water deflector 18 is placed above the microphone port 13. The water deflector 18 advantageously reflects large volumes of water attempting to enter the microphone port 13. The microphone subassembly has an assembly front 15 which resides against the microphone port 13, and an assembly rear 17 which resides within the BTE device case 16.

Figure 3:
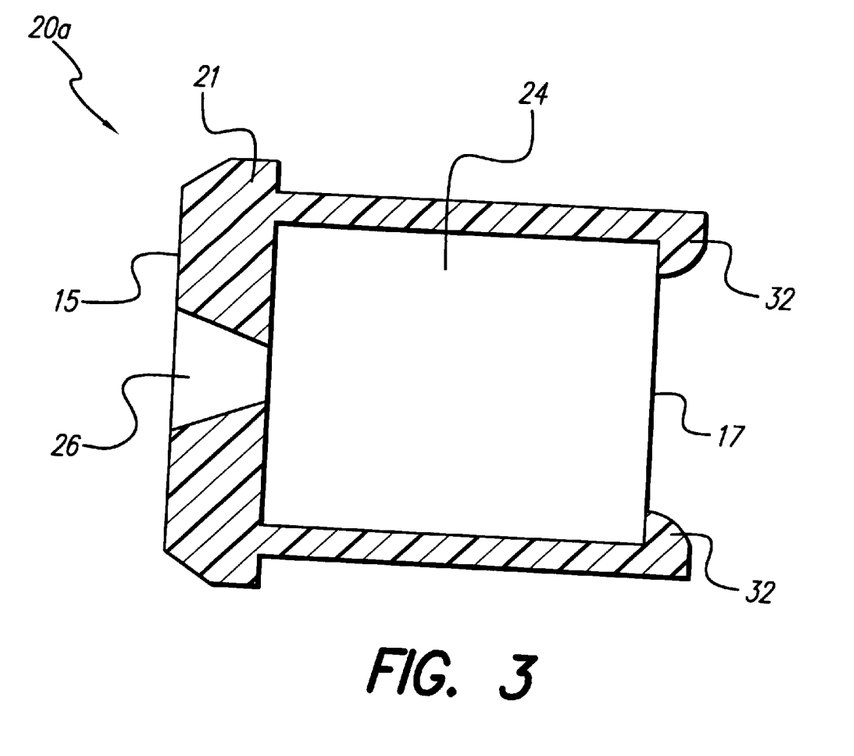
FIG. 3 shows a boot of a microphone subassembly.

A cross-section of a boot 20a of the microphone subassembly 14a is shown in FIG. 3. The microphone subassembly 14a, is comprised of components assembled inside the boot 20a, and the boot 20a is mounted in the BTE case 16. The exterior of the boot 20a is shaped to cooperate with the BTE device case 16 to retain the microphone subassembly 14a in the BTE device case 16. Preferably, a boot shoulder 21 cooperates with an interior part of the BTE device case 16 to retain the microphone subassembly 14 in the BTE device case 16.

The interior of the boot 20a comprises a microphone cavity 24. A sound port 26 provides an opening into the microphone cavity 24. The boot 20a is made from a commercially-available elastomeric material, such as KRATON G2712, or equivalent. The elastomeric material provides isolation from vibrations in the BTE case 16. The sound port 26 extends from the assembly front 15 to the microphone cavity 24. The microphone cavity 24 extends from the sound port 26 to the assembly rear 17. The sound port 26 has the shape of a truncated cone, with a larger diameter, preferably about 0.040 inches, at the assembly front 15, and a smaller diameter, preferably about 0.020 inches where the sound port 26 connects with the microphone cavity 24. When the microphone subassembly 14a is mounted in the BTE case 16, the sound port 26 is aligned with the microphone port 13 to provide an acoustic path for acoustic energy outside the BTE device 10 to enter the sound port 26. The boot also includes boot fingers 32 at the assembly rear 17, which boot fingers 32 partially encroach inwardly into the microphone cavity 24. In a preferred embodiment the boot 20a is round, as is the sound port 26 and the microphone cavity 24. Those skilled in the art will recognize that boots, microphone cavities, and sound ports may be made in a variety of shapes. Such other shapes, or combinations of shapes, are intended to come within the scope of the present invention, as defined in the claims.

Figure 4:
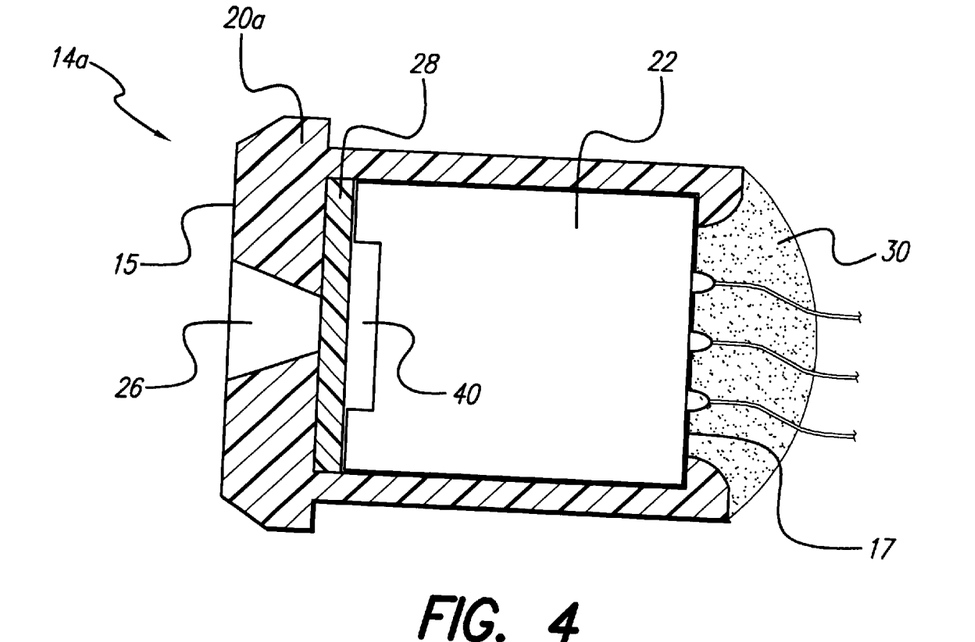
FIG. 4 depicts a cross section of a first embodiment of the microphone subassembly.

The construction of one embodiment of the microphone subassembly 14a is shown in FIG. 4. A microphone 22 resides in the microphone cavity 24. The microphone is preferably cylindrical and about 0.10 inches in diameter. The microphone cavity 24 radially surrounds the microphone 22 and is slightly undersized to provide a moisture-resistant fit between the microphone 22 and the microphone cavity 24. The microphone 22 has a transducer aperture 40, whereby acoustic energy enters the microphone 22. In FIG. 4, and subsequent figures, the transducer apertures are depicted as a rectangular indentation into the microphone 22. In many cases the acoustic aperture may simply be a hole or holes in the microphone 22, and the rectangular indentation shown in the figures is only for purpose of showing the location of the acoustic aperture 40. The present invention is intended to apply to microphones with all shapes of acoustic apertures.

The transducer aperture 40 is aligned with the sound port 26 to allow the acoustic energy entering the boot 20a to travel to the microphone 22. A membrane 28 is positioned between the sound port 26 and the transducer aperture 40. The membrane 28 is manufactured from a commercially-available moisture-resistant material, such as VERSAPOR 10000R, or equivalent. Such material provides resistance to moisture, but still allows acoustic energy to pass. The membrane is preferably round, preferably about 0.10 inches in diameter, and preferably about 0.010 inches thick. The microphone 22 is retained in the microphone cavity 24 by the boot fingers 32 at the rear of the boot 20a. An elastomeric sealant 30 is applied to the assembly rear 17 to provide additional moisture resistance.

Figure 5:
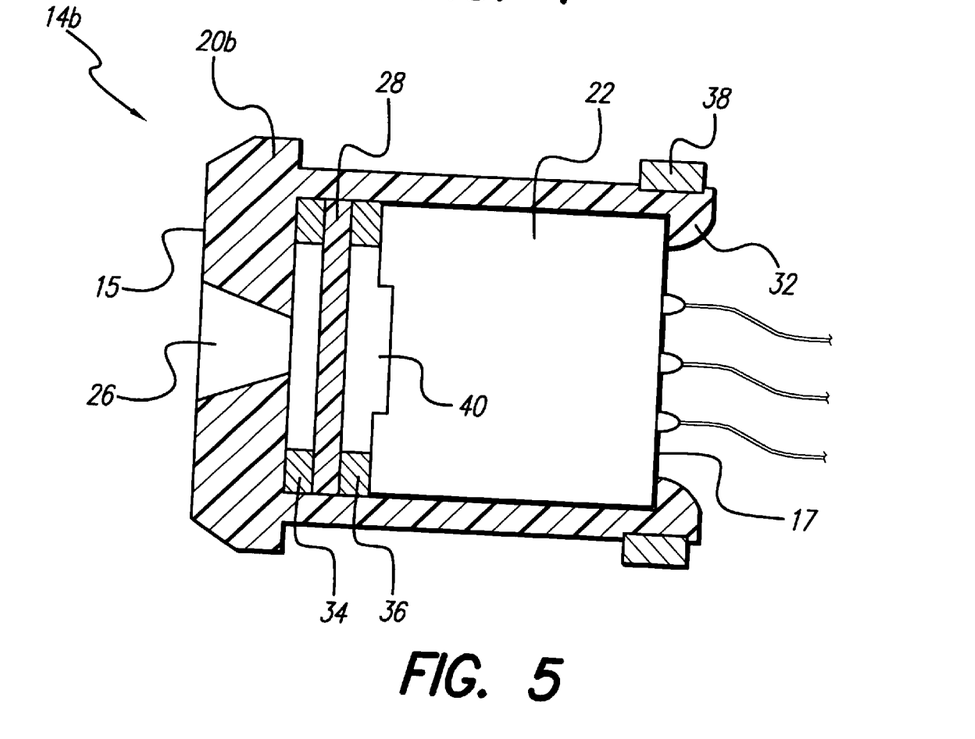
FIG. 5 depicts a cross section of a second embodiment of the microphone subassembly which includes washers in front of and behind the membrane.

A second embodiment of a microphone subassembly 14b is shown in FIG. 5. The microphone subassembly 14b includes a boot 20b similar to the boot 20a in FIG. 4. The boot 20b may be slightly longer than the boot 20a to allow for additional elements. The microphone subassembly 14b includes a first washer 34 and a second washer 36, and a clamp 38. The length of the boot 29b is such that once assembled, the washers 34 and 36, and the membrane 28, are in sufficient longitudinal compression to form a seal. The presence of the membrane 28 in the acoustic path may result in undesirable attenuation of the acoustic energy. A wideband acoustic response is desirable for the microphone subassembly in order to provide more natural sound to the patient. The membrane 28 acts as a series acoustic resistance and the equivalent acoustic volume of the microphone 22 acts as a shunt acoustic capacitance. In order to minimize the effects of the acoustic resistance of the membrane 28 on the wideband acoustic response, the membrane 28 is sandwiched between the first washer 34 and the second washer 36. The inside diameter of the first washer 34 and the inside diameter of the second washer 36, are made large to expose a substantial percentage of the surface area of the membrane 28 to acoustic energy. In a preferred embodiment, the inside diameters of the washers 34, 36 are about 0.07 inches which results in about half (i.e., 49% of the area of a 0.10 inch diameter membrane) of the surface area of the membrane 28 being exposed. The low series acoustic resistance results in a cutoff frequency that is beyond 10 KHz and insures a flat, wideband, acoustic response for the microphone subassembly 14b. The boot 20b is made from high compliance material and the microphone cavity 24 is slightly undersized axially relative to the microphone 22. The first washer 34, membrane 28, and second washer 36, are substantially the same diameter as the microphone 22, which diameter is preferably about 0.10 inches. The first washer 34, membrane 28, and second washer 36 are preferably about 0.010 inches thick. The microphone subassembly 14b is assembled by pushing the first washer 34, membrane 28, second washer 36, and microphone 22 into the microphone cavity 24. The boot fingers 32 press against the microphone 22, thus retaining the microphone 22 in the microphone cavity 24. A ring shaped clamp 38 resides on the exterior of the boot 20b, over the boot fingers 32, thereby increasing the retaining force that the boot fingers 32 apply to the microphone 22.

Figure 6:
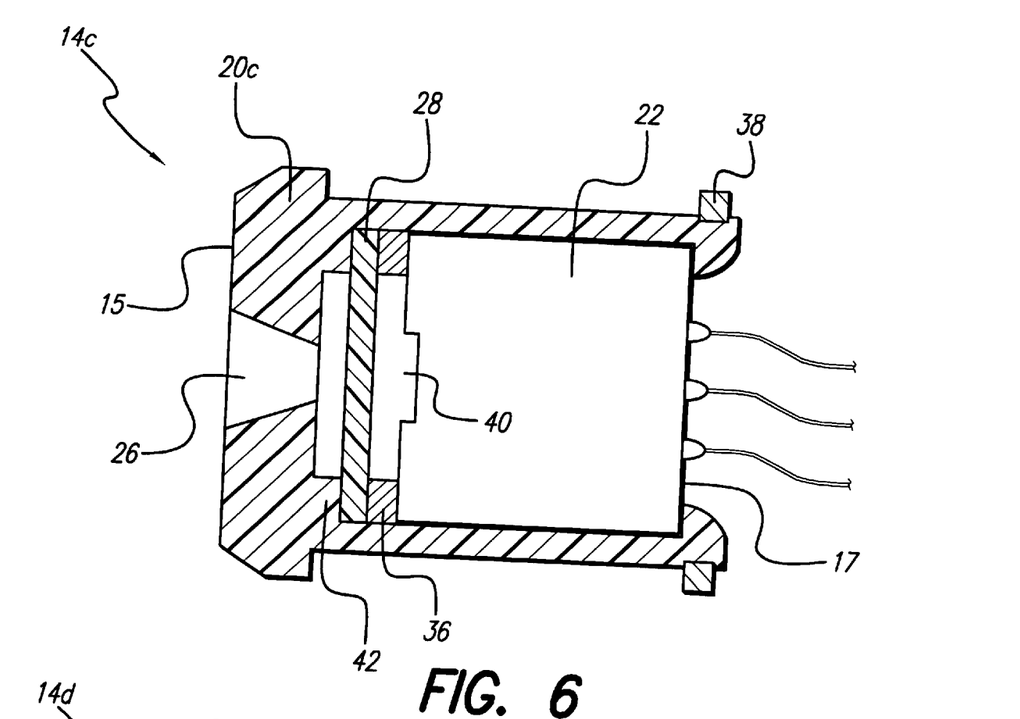
FIG. 6 depicts a cross section of a third embodiment of the microphone subassembly which replaces the washer in front of the membrane with a step in the microphone cavity.

Yet another embodiment of a microphone subassembly 14c is shown in FIG. 6. The microphone subassembly 14c utilizes a third boot 20c similar to the boot 20b in FIG. 5. However, the boot 20c replaces the washer 34 by providing a cavity step 42 between the membrane 28 and the sound port 26. The use of the cavity step 42 advantageously eliminates one step in the assembly of the microphone subassembly 14c. The length of the boot 29c is such that once assembled, the washer 36 and the membrane 28, are in sufficient longitudinal compression to form a seal.

Figure 7:
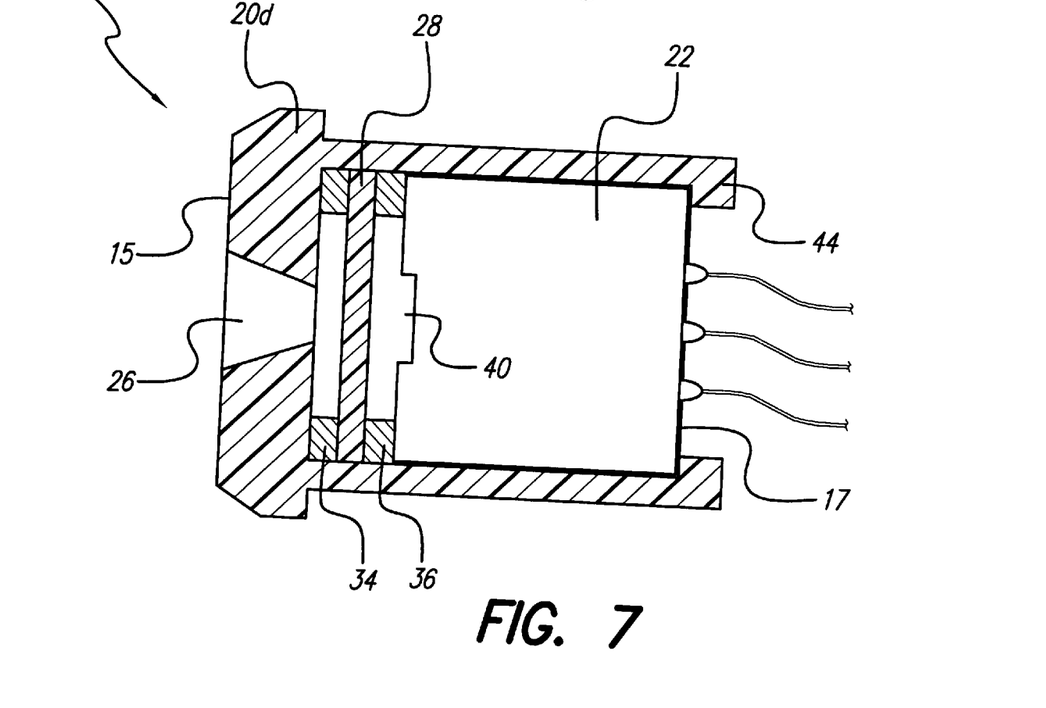
FIG. 7 depicts a cross section of a fourth embodiment of the microphone subassembly with a retaining flange to retain the microphone in the microphone cavity.

A fourth embodiment of a microphone subassembly 14d is shown in FIG. 7. The microphone subassembly 14d includes a fourth boot 20d. The boot 20d is identical to the boot 20b shown in FIG. 5 with the single exception that the boot fingers 32 have been replaced by a retaining flange 44. The retaining flange 44 wraps around the opening of the microphone cavity 24. The length of the boot 29d is such that once assembled, the washers 34 and 36, and the membrane 28, are in sufficient longitudinal compression to form a seal.

The four embodiments described in FIGS. 4, 5, 6, and 7 include microphone subassemblies that are assembled by pressing a combination of washers, membranes, and microphones into a microphone cavity, wherein the washers, membranes, and microphones are kept in place by either the boot fingers 32, or retaining flange 44. Various other embodiments include elements identical to those recited for FIGS. 4, 5, 6, and 7, but vary by the addition of an attaching means exercised on the interfaces between the boot, washers, membranes, and/or microphones. The attaching means may be an adhesive or a thermal or ultrasonic bonding process. Any suitable commercially-available bonding agent or compound may be used, as long as the agent or compound is compatible with the boot, membrane, or washer material. Agents or compounds that are absorbed by the boot, membrane, or washer material, and substantially alter the physical characteristics of the material, would not be suitable. In one embodiment of a microphone subassembly, similar to the microphone subassembly 14a shown in FIG. 4, the attaching means is exercised between the boot 20a and the membrane 28, thereby attaching the membrane 28 to the boot 20a. In another embodiment of a microphone subassembly, also similar to the microphone subassembly 14a shown in FIG. 4, the attaching means is exercised between the microphone 22 and the membrane 28, thereby attaching the membrane 28 to the microphone 22. Various other embodiments of the application of attaching means to the boot, washers, membranes, and/or microphones will be apparent to those skilled in the art and are intended to come within the scope of the present invention.

Figure 8:
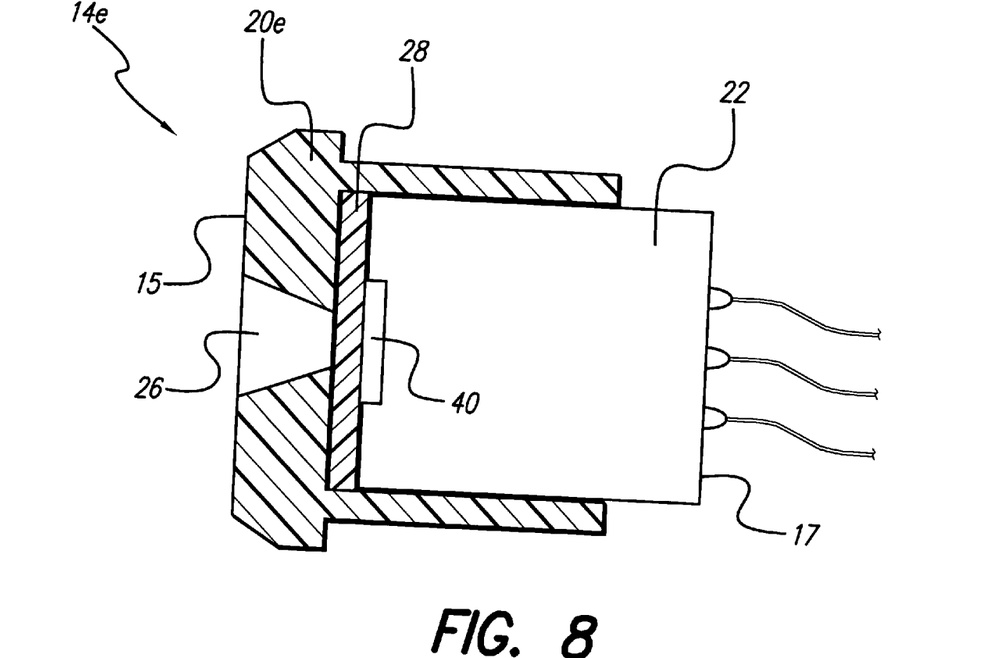
FIG. 8 illustrates a microphone subassembly with a boot which partially extends over the microphone.

The embodiments of a microphone subassembly described above all include a boot which extends over the length of the microphone. A fifth embodiment of a microphone subassembly 14e, includes a partial boot 20e that only partially extends over the microphone 22, as shown in FIG. 8. The microphone subassembly 14e is very similar to the microphone subassembly 14a in FIG. 4. Other embodiments of a microphone subassembly with a partial boot could also include one or two washers 34, 36, or a cavity step 42 as shown in FIGS. 5 and 6. The microphone 22 could be retained by a friction fit, or held in by an adhesive.

Figure 9:
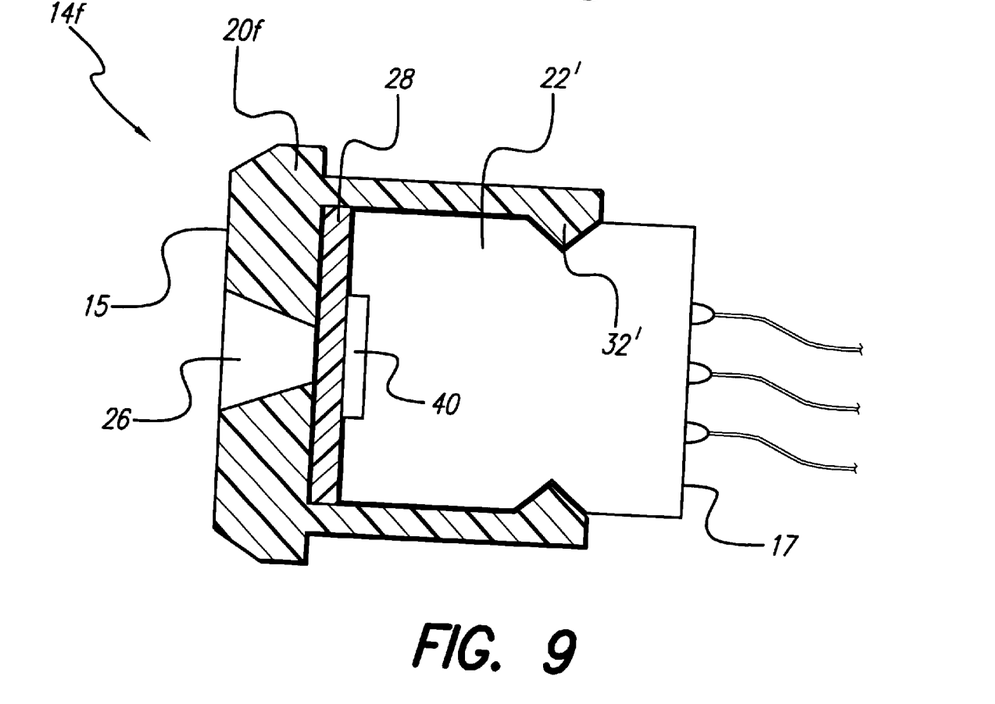
FIG. 9 shows an embodiment of the partial boot with a retaining means and a microphone including cooperating surfaces.

A microphone subassembly 14f, which includes a second partial boot 20f with a cooperating microphone 22', is shown in FIG. 9. The partial boot 20f includes at least two second boot fingers 32' that cooperate with the microphone 22' to retain the microphone 22' in the boot 20f. As in the case of the microphone subassembly 14e, the microphone subassembly 14f may be practiced with one or two washers 34 and 36, and/or the cavity step 42 shown in FIGS. 5 and 6.

Figure 10:
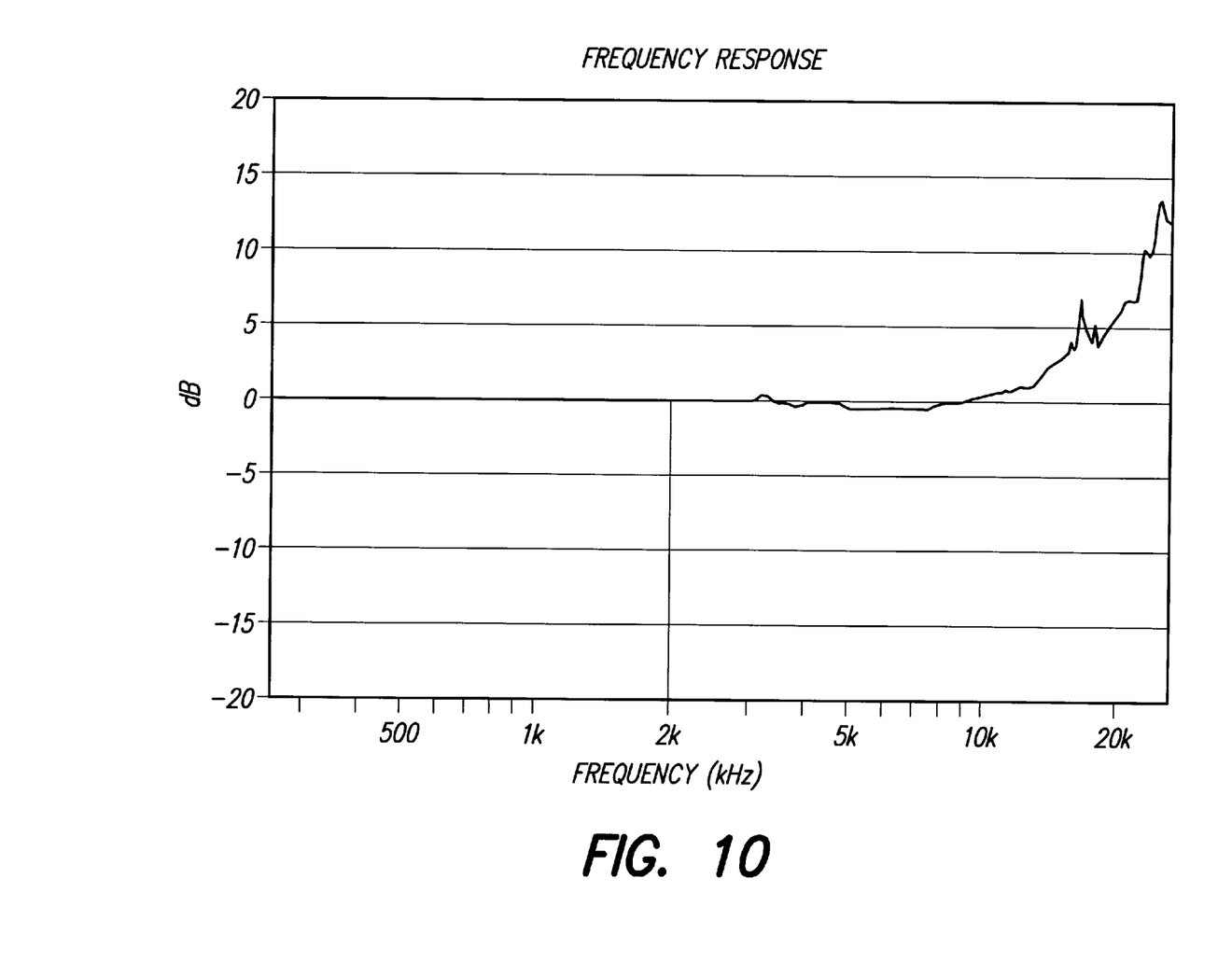
FIG. 10 shows the frequency response of the microphone subassembly for a preferred embodiment.

A representative plot of the frequency response of the microphone subassemblies 14b, 14c, and 14d is shown in FIG. 10. As can be seen in the plot, the frequency response is substantially flat beyond 10 KHz. (Note, the response shown in FIG. 10 is actually an inverse response, thus the response is shown as measuring beyond 10 KHz, whereas the actual (non-inverse) response would decrease beyond 10 KHz).

Those skilled in the art will recognize that the present invention may be practiced in many microphone subassembly configurations. The heart of the present invention is the use of a moisture-resistant membrane, and/or a subassembly construction utilizing a combination of washers and membrane, that provide both moisture resistance and/or wideband frequency response. An embodiment comprising variations to boot shape, microphone cavity shape, microphone retention means, sound port configuration, or other details, is intended to fall within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. A moisture-resistant microphone subassembly for a behind-the-ear (BTE) hearing device, the microphone subassembly comprising:
    a boot including a sound port and a microphone cavity, wherein the boot has a boot front, and wherein the sound port comprises an aperture in the boot front, and wherein the sound port connects with the microphone cavity;
    a microphone, wherein the microphone includes a microphone body and a transducer aperture, and wherein at least part of the microphone resides in the microphone cavity, wherein the microphone is positioned within the microphone cavity so that the transducer aperture may receive acoustic energy passing through the sound port, and wherein the boot provides a moisture-resistant seal around the microphone body, preventing moisture from reaching the transducer aperture by passing between the boot and the microphone body of the microphone;
    a membrane positioned between the sound port and the transducer aperture, wherein the membrane prevents moisture from reaching the transducer aperture through the sound port.

2. The microphone subassembly of claim 1 wherein the membrane provides a second moisture-resistant seal between the sound port and the transducer aperture.

3. The microphone subassembly of claim 2 wherein the microphone resides completely within the microphone cavity wherein the boot is constructed of a compliant material, and wherein the microphone body has at least one microphone cross sectional shape, and wherein the boot has a boot rear opposite the boot front, and wherein the microphone cavity extends from the sound port to the boot rear, and wherein the microphone cavity has at least one cavity cross sectional shape, and wherein the at least one cavity cross sectional shape substantially matches the at least one microphone cross sectional shape adjacent to the at least one cavity cross sectional shape when the microphone is residing in the microphone cavity.

4. The microphone subassembly of claim 3 wherein the boot further includes at least two boot fingers, wherein the at least two boot fingers are at the boot rear, and wherein the at least two boot fingers retain the microphone in the microphone cavity.

5. The microphone subassembly of claim 4 wherein the microphone subassembly further includes a sealant at the boot rear, and wherein the sealant seals the microphone cavity.

6. The microphone subassembly of claim 5 wherein the microphone cavity has a cavity forward end, and wherein the sound port connects with the microphone cavity at the cavity forward end, and wherein the membrane resides in the cavity forward end.

7. The microphone subassembly of claim 6 wherein the membrane is attached to the cavity forward end by a member of a group consisting of an adhesive, a thermal bonding process, and an ultrasonic bonding process.

8. The microphone subassembly of claim 5 wherein the membrane is attached to the microphone.

9. The microphone subassembly of claim 8 wherein the membrane is attached to the microphone by a member of a group consisting of an adhesive, a thermal bonding process, and an ultrasonic bonding process.

10. The microphone subassembly of claim 4 wherein the microphone subassembly further includes a first washer and a second washer, wherein the first washer resides against the membrane on the side of the membrane facing the sound port, and wherein the second washer resides between the membrane and the microphone.

11. The microphone subassembly of claim 10 wherein the microphone subassembly further includes a clamp, wherein the clamp resides around the exterior of the boot and wherein the clamp applies force on the boot fingers, thereby applying retaining force to the rear of the microphone.

12. The microphone subassembly of claim 1 wherein the microphone has a microphone length and a microphone cross sectional shape, and wherein the microphone cross sectional shape is uniform over the microphone length, and wherein the microphone cavity has a cavity length, and wherein the cross sectional shape of the microphone cavity is uniform over the cavity length.

13. The microphone subassembly of claim 12 wherein the boot has a boot rear opposite the boot front, and wherein the boot further includes at least two boot fingers, wherein the at least two boot fingers are at the boot rear, and wherein the at least two boot fingers retain the microphone in the microphone cavity.

14. The microphone subassembly of claim 12 wherein the boot has a boot rear opposite the boot front, and wherein the boot includes a retaining flange, wherein the retaining flange is at the boot rear, and wherein the retaining flange retains the microphone in the microphone cavity.

15. The microphone subassembly of claim 12 wherein the microphone cavity has a cavity forward end nearest the sound port and at least one cavity cross sectional shape, and wherein the microphone subassembly further includes a first washer and a second washer, and wherein:
    the first washer resides within the microphone cavity, wherein the first washer is positioned directly against the cavity forward end, and wherein the first washer is shaped to match the at least one cavity cross sectional shape at the location within the microphone cavity where the first washer resides;
    the membrane resides within the microphone cavity, wherein the membrane is positioned directly against the first washer, and wherein the membrane is shaped to match the at least one cavity cross sectional shape at the location within the microphone cavity where the membrane resides;
    the second washer resides within the microphone cavity, wherein the second washer is positioned directly against the membrane, and wherein the second washer is shaped to match the at least one cavity cross sectional shape at the location within the microphone cavity where the second washer resides; and
    the microphone is positioned directly against the second washer.

16. The microphone subassembly of claim 15 wherein the first washer and the second washer have inside diameters, and wherein the inside diameters are about 70 percent of the diameter of the membrane.

17. The microphone subassembly of claim 15 wherein at least two of the set consisting of the boot, the first washer, the membrane, the second washer, and the microphone are attached to each other using an adhesive, a thermal bonding process, or an ultrasonic bonding process.

18. The microphone subassembly of claim 1 wherein the microphone cavity has a cavity forward end nearest the sound port and at least one cavity cross sectional shape, and wherein the microphone cavity includes a cavity step, and wherein the microphone subassembly further includes a second washer, and wherein:

the cavity step is within the microphone cavity, wherein the cavity step is located directly at the cavity forward end, and wherein the cavity step comprises a reduction in the inside dimension of the microphone cavity;

the membrane resides within the microphone cavity, wherein the membrane is positioned directly against the cavity step, and wherein the membrane is shaped to match the at least one cavity cross sectional shape at the location within the microphone cavity where the membrane resides;

the second washer resides within the microphone cavity, wherein the second washer is positioned directly against the membrane, and wherein the second washer is shaped to match the at least one cavity cross sectional shape at the location within the microphone cavity where the second washer resides; and the microphone is positioned directly against the second washer.

19. The microphone subassembly of claim 18 wherein the aperture resulting from the cavity step, and the aperture in the second washer each have an opening that has a cross-sectional area that is about half of the area of the microphone cavity cross sectional shape.

20. The microphone subassembly of claim 1 wherein the BTE hearing device comprises an exterior part of an Implantable Cochlear Stimulation System.

21. The microphone subassembly of claim 1 wherein the BTE hearing device includes an arch that reaches above an ear of the patient, wherein the microphone assembly resides in the BTE hearing device near the highest point of the arch.

22. The microphone subassembly of claim 1 wherein the BTE hearing device includes a BTE case, and wherein the BTE case includes a microphone port, and wherein the microphone subassembly resides within the BTE case, and wherein the sound port is aligned with the microphone port so that acoustic energy may pass through the microphone port and into the sound port, and wherein the BTE case further includes a water deflector protruding from the BTE case, wherein the water deflector is positioned above the microphone port.

23. A microphone subassembly for a Behind-The-Ear (BTE) hearing device, the microphone subassembly comprising:

a microphone including a transducer aperture;
means for attaching the microphone to the subassembly;
means for providing an acoustic path to the transducer aperture;
means for preventing moisture from reaching the transducer aperture along the acoustic path, wherein the means for preventing moisture from reaching the transducer aperture along the acoustic path allows acoustic energy to reach the transducer aperture along the acoustic path;
means for providing a moisture-resistant seal for the microphone wherein the moisture-resistant seal seals the transducer aperture from moisture entering the transducer aperture from paths other then the acoustic path; and
means for mounting the microphone subassembly in the BTE hearing device.

24. The microphone subassembly of claim 23 wherein the BTE hearing device includes a BTE case, and wherein the means for mounting the microphone subassembly in the BTE hearing device comprises a shape of the exterior of the microphone subassembly which cooperates with the BTE case.

25. The microphone subassembly of claim 24 wherein the microphone subassembly includes means for providing vibration isolation of the microphone from the BTE case.

26. The microphone subassembly of claim 23 wherein the BTE hearing device includes a BTE case, and wherein the means for mounting the microphone subassembly comprises protruding surfaces on the exterior of the microphone subassembly, and wherein the protruding surfaces engage mating surfaces in the BTE case.

27. The microphone subassembly of claim 23 wherein the means for providing a moisture-resistant seal is a boot, and wherein the boot radially surrounds the microphone.

28. The microphone subassembly of claim 23 wherein the means for preventing moisture from reaching the transducer aperture along the acoustic path comprises a moisture-resistant membrane.

29. The microphone subassembly of claim 23 wherein the microphone subassembly includes a boot, and wherein the boot includes a microphone cavity and a sound port, wherein the sound port connects to the microphone cavity, and wherein the microphone resides in the microphone cavity, and wherein the transducer aperture is aligned with the sound port, and thereby provides the means for providing an acoustic path.

30. The microphone subassembly of claim 29 wherein the boot includes boot fingers, and wherein the means for attaching the microphone to the subassembly includes the boot fingers that retain the microphone within the microphone cavity.

31. The microphone subassembly of claim 30 wherein the means for attaching the microphone to the subassembly further includes a clamp, wherein the clamp is positioned on the outside of the boot, and wherein the clamp retains the boot fingers in a position wherein the boot fingers exert the retaining force upon the microphone.

32. The microphone subassembly of claim 29 wherein the boot has a microphone cavity opening, wherein the microphone is insertable into the microphone cavity through the microphone cavity opening, and wherein elastomeric sealant is applied to the microphone cavity opening after the microphone has been inserted into the microphone cavity, and wherein the elastomeric sealant provides the means for attaching the microphone to the subassembly.

33. The microphone subassembly of claim 29 wherein the boot includes a retaining flange, and, wherein the retaining flange retains the microphone within the microphone cavity.

34. The microphone subassembly of claim 29 wherein the means for preventing moisture from reaching the transducer aperture is a moisture-resistant membrane, and wherein the membrane resides in the microphone cavity between the sound port and the transducer aperture.

35. The microphone subassembly of claim 34 wherein the microphone subassembly further includes a first washer and a second washer, and wherein the first washer resides between the sound port and the membrane, and wherein the second washer resides between the membrane and the transducer aperture.

36. The microphone subassembly of claim 35 wherein the first washer and the second washer are made of a high-compliance material.

37. The microphone subassembly of claim 36 wherein the first washer and the second washer have an outside diameter and an inside diameter, wherein the outside diameter is matched to the microphone cavity, and wherein the inside diameter is sufficiently large to expose a substantial percentage of the surface of the membrane.

38. The microphone subassembly of claim 37 wherein the inside diameter exposes forty nine percent of the membrane.

39. The microphone subassembly of claim 35 wherein at least two of the set consisting of the boot, the first washer, the membrane, the second washer, and the microphone are attached to each other by a member of a group consisting of an adhesive, a thermal bonding process, and an ultrasonic bonding process.

40. The microphone subassembly of claim 34 wherein the microphone cavity includes a cavity step, wherein the cavity step resides between the membrane and the sound port, and wherein the microphone subassembly further includes a second washer, wherein the second washer resides between the membrane and the transducer aperture.

41. The microphone subassembly of claim 40 wherein the cavity step has an step inside diameter, and wherein the step inside diameter is sufficiently large to expose a substantial percentage of the surface of the membrane, and wherein the second washer has an outside diameter and an inside diameter, wherein the outside diameter is matched to the microphone cavity, and wherein the inside diameter is sufficiently large to expose a substantial percentage of the surface of the membrane.

42. The microphone subassembly of claim 41 wherein the step inside diameter exposes forty nine percent of the membrane, and wherein the inside diameter of the second washer exposes forty nine percent of the membrane.

43. The microphone subassembly of claim 40 wherein at least two of the set consisting of the cavity step, the membrane, the second washer, and the microphone are attached to each other by a member of a group consisting of an adhesive, a thermal bonding process, and an ultrasonic bonding process.

44. The microphone subassembly of claim 23 wherein the BTE hearing device is part of an Implantable Cochlear System.

45. A method for constructing a moisture-resistant microphone subassembly for a BTE hearing device, comprising the steps of:
   attaching a microphone to the microphone subassembly, wherein the microphone includes an transducer aperture;
   providing an acoustic path to the transducer aperture;
   preventing moisture from reaching the transducer aperture along the acoustic path, wherein the means for preventing moisture from reaching the transducer aperture along the acoustic path allows acoustic energy to reach the transducer aperture along the acoustic path;
   providing a moisture-resistant seal for the microphone wherein the moisture-resistant seal seals the transducer aperture from moisture entering the transducer aperture from all paths other than the acoustic path; and
   mounting the microphone subassembly in the BTE hearing device.

46. The method of claim 45 wherein mounting the microphone subassembly in the BTE hearing device comprises mounting the microphone subassembly in the BTE hearing device of an Implantable Cochlear System.

47. The method of claim 45 wherein attaching a microphone to the subassembly comprises:
   providing a boot, wherein the boot includes a microphone cavity, and wherein the microphone is insertable into the microphone cavity; and
   inserting the microphone into the microphone cavity.

48. The method of claim 45 wherein providing an acoustic path comprises providing a boot, wherein the boot includes a microphone cavity and a sound port, wherein the sound port connects to the microphone cavity, and wherein the microphone is insertable into the microphone cavity; whereby acoustic energy may pass through the sound port and to the transducer aperture.

49. The method of claim 45 wherein preventing moisture from reaching the transducer aperture comprises placing a membrane in the acoustic path, wherein the membrane resists the passage of moisture along the acoustic past, but allows acoustic energy to reach the transducer aperture along the acoustic path.

50. The method of claim 45 wherein providing a moisture-resistant seal comprises providing a boot with a microphone cavity, wherein the microphone is insertable into the microphone cavity, and wherein the microphone to microphone cavity fit provides a moisture-resistant seal.

* * * * *